(12) United States Patent
Kline (10) Patent No.: US 9,320,465 B2
(45) Date of Patent: Apr. 26, 2016

(54) BIO-CHIPS AND NANO-BIOCHIPS

(75) Inventor: Eric V. Kline, Rochester, MN (US)

(73) Assignee: International Business Machines Corporation, Armonk, NY (US)

(*) Notice: Subject to any disclaimer, the term of this patent is extended or adjusted under 35 U.S.C. 154(b) by 821 days.

(21) Appl. No.: 13/532,375

(22) Filed: Jun. 25, 2012

(65) Prior Publication Data

US 2013/0345525 A1    Dec. 26, 2013

(51) Int. Cl.
| | |
|---|---|
| A61B 5/07 | (2006.01) |
| A61B 5/1473 | (2006.01) |
| A61B 8/08 | (2006.01) |
| A61B 8/12 | (2006.01) |
| A61B 5/145 | (2006.01) |

(52) U.S. Cl.
CPC .......... *A61B 5/1473* (2013.01); *A61B 5/07* (2013.01); *A61B 5/14503* (2013.01); *A61B 5/14507* (2013.01); *A61B 8/085* (2013.01); *A61B 8/12* (2013.01); *A61B 2562/16* (2013.01)

(58) Field of Classification Search
CPC .. A61B 2562/16; A61B 5/07; A61B 5/14503; A61B 5/14507; A61B 5/1473; A61B 8/085; A61B 8/12
USPC ........................................................ 600/302
See application file for complete search history.

(56) References Cited

U.S. PATENT DOCUMENTS

| | | | |
|---|---|---|---|
| 6,259,937 B1 | 7/2001 | Schulman et al. | |
| 6,402,689 B1 | 6/2002 | Scarantino et al. | |
| 6,544,193 B2 * | 4/2003 | Abreu | 600/558 |
| 6,770,725 B2 | 8/2004 | Santerre | |
| 6,829,498 B2 | 12/2004 | Kipke et al. | |
| 7,040,756 B2 | 5/2006 | Qiu et al. | |
| 7,118,531 B2 | 10/2006 | Krill | |
| 7,171,252 B1 | 1/2007 | Scarantino et al. | |
| 7,192,398 B2 | 3/2007 | Feliss et al. | |
| 7,479,108 B2 | 1/2009 | Rini et al. | |
| 7,534,207 B2 | 5/2009 | Shehada et al. | |
| 7,637,868 B2 | 12/2009 | Saint et al. | |
| 7,662,864 B2 | 2/2010 | Kanamathareddy et al. | |
| 7,809,441 B2 | 10/2010 | Kane et al. | |
| 7,833,474 B2 | 11/2010 | Swanson et al. | |
| 7,884,171 B2 | 2/2011 | Ward et al. | |
| 7,920,907 B2 | 4/2011 | McGarraugh et al. | |
| 7,937,148 B2 | 5/2011 | Jacobson | |
| 7,985,386 B2 | 7/2011 | Santini, Jr. et al. | |
| 8,005,526 B2 | 8/2011 | Martin et al. | |
| 8,012,587 B2 | 9/2011 | Gedig et al. | |
| 8,032,218 B2 | 10/2011 | Wong et al. | |

(Continued)

OTHER PUBLICATIONS http://artificialretina.energy.gov/technologies.shtml accessed on Feb. 16, 2012, Artificial Retina Project Restoring Sight Through Science, Biological and Environmental Research Program of the U.S. Department of Energy Office of Science, pp. 1-9, last modified Sep. 3, 2009.

(Continued)

*Primary Examiner* — Navin Natnithithadha
*Assistant Examiner* — Eric Messersmith
(74) *Attorney, Agent, or Firm* — Scully, Scott, Murphy & Presser, P.C.; Damion Josephs, Esq.

(57) ABSTRACT

A biochip and nanochip device, or a system of biochips, providing diagnostic testing, sensing and therapeutic functionality useful in diagnosis and treatment of a variety of physiological maladies.

7 Claims, 5 Drawing Sheets

(56) References Cited

U.S. PATENT DOCUMENTS

| | | | |
|---|---|---|---|
| 8,065,000 B2 | 11/2011 | Salo et al. | |
| 2005/0008676 A1 | 1/2005 | Qiu et al. | |
| 2006/0009805 A1 | 1/2006 | Jensen et al. | |
| 2007/0112261 A1* | 5/2007 | Enegren et al. | 600/365 |
| 2009/0182388 A1* | 7/2009 | Von Arx et al. | 607/5 |
| 2009/0232700 A1 | 9/2009 | Alarcon et al. | |
| 2010/0285084 A1 | 11/2010 | Yang et al. | |
| 2011/0021347 A1 | 1/2011 | Ugajin et al. | |
| 2011/0301665 A1 | 12/2011 | Mercanzini et al. | |
| 2013/0053671 A1* | 2/2013 | Farra | 600/377 |

OTHER PUBLICATIONS

Schroeder, M. J., et al., "An Analysis on the Role of Water Content and State on Effective Permittivity Using Mising Formulas", Journal of Biomechanics, Biomedical and Biophysical Engineering, 2(1):1-11 (2008).

http://www.sciencedaily.com/releases/2006/04/060424111927.htm accessed on Feb. 15, 2012, University of Utah to Help Build Realistic Bionic Arm, Science Daily, pp. 1-4, Apr. 24, 2006.

http://www.sciencedaily.com/releases/2010/12/101214181928.htm accessed on Feb. 15, 2012, Robot Arm Improves Performance of Brain-Controlled Device, Science Direct, pp. 1-2 (only p. 1 submitted), Dec. 14, 2010.

http://www.sciencedaily.com/releases/2007/11/071111182522.htm accessed Feb. 15, 2012, Thinking Makes It So: Science Extends Reach of Prosthetic Arms, Science Direct,, pp. 1-2 (only p. 1 submitted) Nov. 11, 2007.

http://www.sciencedaily.com/releases/2009/10/091014122043.htm accessed on Feb. 15, 2012, Bioengineering of Nerve-Muscle Connection Could Improve Hand Use for Wounded Soldiers, Science Direct, p. 1, Oct. 14, 2009.

Skourou, C., et al., "Tissue permittivity a monitor for progressive tissue fibrosis as observed in bystander tissues following experimental high dose rate irradiation", Cancer Biology & Therapy 8(23):2221-2227, Dec. 1, 2009.

http://en.wikipedia.org/wiki/Organic_semiconductor accessed on Feb. 15, 2012, Organic Semiconductor, pp. 1-5, last modified on Jan. 26, 2012.

* cited by examiner

BIO-CHIPS AND NANO-BIOCHIPS

BACKGROUND OF THE DISCLOSURE

The present disclosure relates to biochips, generally, and more particularly, a biochip and nanochip device providing diagnostic testing, sensing and therapeutic functionality useful in diagnosis and treatment of a variety of physiological maladies.

BRIEF SUMMARY OF THE DISCLOSURE

Biocompatible chip (Bio-chip) or nanochip device implementing semiconductor and (Micro-Electro-Mechanical Systems) technologies for use in providing therapeutic regiments to various human diseases. The disclosure describes embodiments for sensing (afferent) operating biochips; active functioning (efferent) operating biochips; and nano-biochips which would be encapsulated in a host cell or non-antigenic membrane. The sensing (afferent) operating biochip and the active functioning (efferent) operating biochip includes various embodiments.

Thus, in one aspect, there is provided a biocompatible microchip for diagnosis or monitoring of a medical condition in a subject. The microchip comprises: a housing including a biocompatible coating or covering, a first semiconductor substrate situated in the housing upon which is located one or more sensor devices for sensing conditions and providing measurements within the subject; a second semiconductor substrate situated in the housing including a programmed control unit and an associated memory block configured for controlling operations on the microchip in response to received external command or a sensed condition within the subject; a communications sub-system situated in the housing including one or more communications devices for transmitting signals to and receiving signals from a communications receiver device external to the subject; a plurality of storage vessels for storing therapeutic or diagnostic materials; and an output fluid connector partially housed in the housing in fluid communication with the one or more the storage vessels for outputting the therapeutic or diagnostic materials under control of the programmed control unit.

Further to this aspect, the biocompatible microchip further comprises an input fluid connector partially housed in the housing and under programmed control for obtaining one or more biological samples from the subject, wherein one or more of the plurality of storage vessels provide a reactant for reaction with a received biological sample in a reactant chamber located within the housing; and, the programmed controller causing a sensor device to sense a resulting condition of the reacted biological sample in the reactant chamber resulting according to the reaction.

In a further aspect, a biocompatible nanochip for treatment of a medical condition in a subject comprises: a semiconductor substrate upon which is located: one or more sensor devices for sensing conditions and providing measurements within the subject, a programmed control unit and an associated memory block configured for controlling operations on the nanochip in response to received external command or a sensed condition within the subject; and, a communications sub-system including one or more communications devices for transmitting signals to and receiving signals from a communications receiver device external to the subject; a power source for powering the communications sub-system and the programmed control unit; and, an external biocompatible coating or covering for the semiconductor substrate.

The nanochip has a length, width and height dimension of less than 5 µm.

DETAILED DESCRIPTION

Many medical conditions exist for which biocompatible microprocessors and nano-microprocessors could be useful diagnostic, therapeutic, and/or adjunct therapeutic devices. This disclosure provides novel bio-chips and nano-biochips useful in diagnosis and treatment of a variety of physiologic pathologies.

This disclosure provides biochips with three distinct parameters. The three parameters relate to biochip: 1) position within the subject (either fixed or mobile); 2) topology (whether the biochip is stand-alone or operates as part of a system); and 3) mode of operation (sensing (afferent) or driving (efferent)). The three variables are linearly combined to yield eight biochip configurations.

In one example, an independent, stationary biochip with one or more sensing functions is provided. In another example, a plurality of interdependent, stationary biochips with interconnected sensing functions is provided. In a further example, an independent, mobile biochip with one or more sensing functions is provided. In an additional example, a plurality of interdependent, mobile biochips with interconnected sensing functions is provided. In another example, an independent, stationary biochip with one or more driving functions is provided. In yet another example, a plurality of interdependent, stationary biochips with interconnected driving functions is provided. In a further example, an independent, mobile biochip with one or more driving functions is provided. In an additional example, a plurality of interdependent, mobile biochips with interconnected driving functions is provided.

Figure 1:
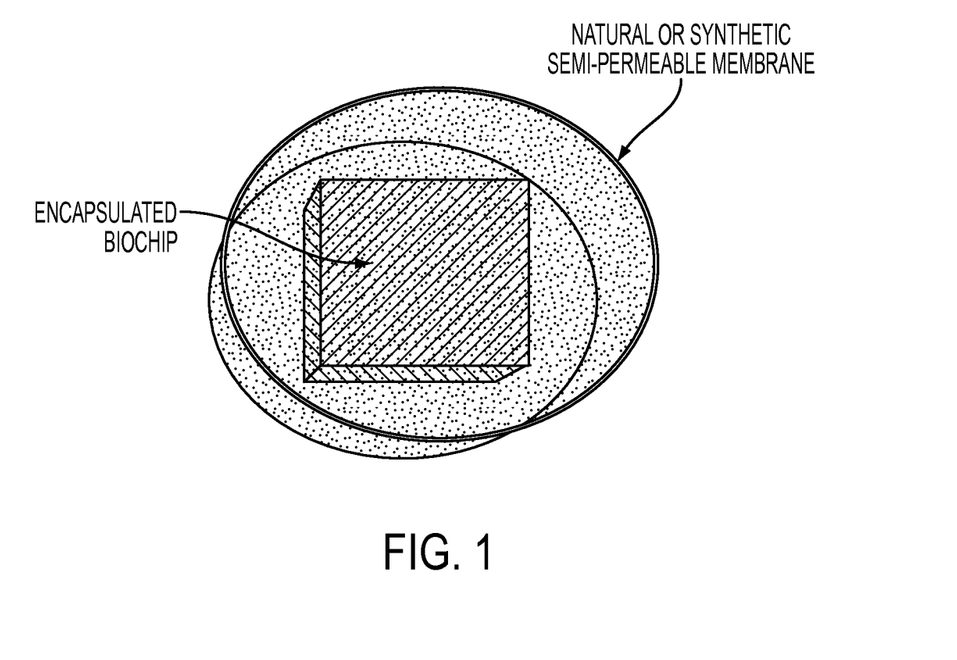
FIG. 1. Exemplary Encapsulation of Nano-Biochip in Cell or Liposomal Membrane.
Figure 2A:
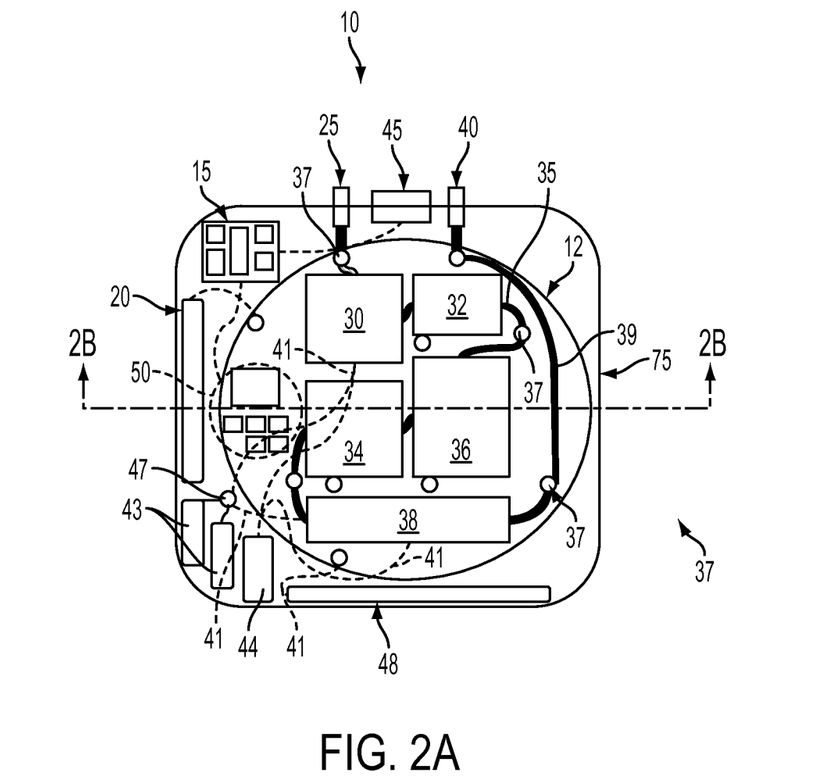
FIG. 2A depicts an exposed, top view of a biochip 10 according to one embodiment.
Figure 2B:
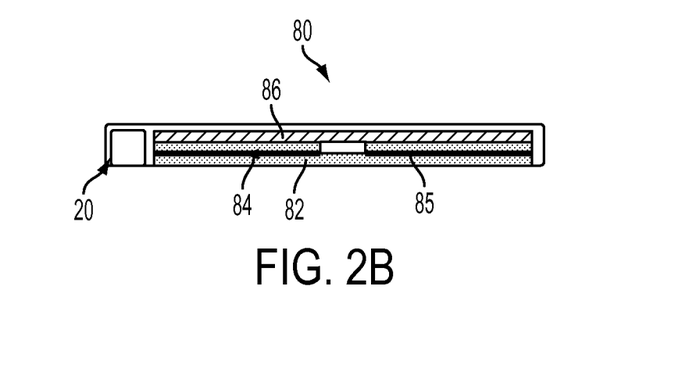
FIG. 2B depicts a cross-sectional view taken along line 2B-2B of FIG. 2A. according to one embodiment.

FIG. 2A shows an embodiment of an implantable afferent or efferent biochip module 10 ("module") configured to enable the allowable matrix of biochip states and functions. In particular, module 10 includes a bio-compatible package 75 housing components such as: a semiconductor material substrate (e.g., silicon or type III-IV material substrates) wafer or substrate 12 having formed thereon a plurality of systems including elements (e.g., active and passive device) configured to perform the sensing and active driving functions; and, a power supply 15 including a power source such as a battery 20 for providing the power to the configured elements. Further, optionally included in module 10 is an external connector 45 adapted to provide power (such as electric current) to the power supply device within packaging 75 from an external power source, such as a battery or generator, for performing biochip functions. Alternately, the external connector 45 is an electrical connector for wire based communication between module and an external control or processing node. The connector 45 may also be or include a mechanical connector for fluid communication, for example, to accept fresh reagents and/or flush wastes. The biochip module 10 may be of a size on the order of about 10 mm to 50 mm on a side housing the wafer 12 and additional configured elements for a single chip or small module embodiment, while larger modules (such as illustrated in FIGS. 2A and 2B) are on the order of about 100 to 200 mm on a side housing the wafer 12 and additional configured elements.

The packaging 75 can have a coating of a bio-compatible metal, such as alumina, zirconia, or alloys of alumina and/or zirconia, or other bio-compatible substances such as poly (ethylene glycol) or polytetrafluoroethylene-like materials with thicknesses ranging from between 0.5 µm and 20 µm. The biochips are on the order of 10 to 50 mm on a side; nanobiochips are <5 microns on a side; the coating/membrane thickness may range anywhere between about 20 and 800 microinches. Alternatively, the packaging can be a composite material including but not limited to insulating materials, water-vapor permeable materials, and polymeric materials, such as epoxies, urethanes, silicones, resins, Parylene, and the like. The packaging can be a polymer comprising hydrophobic, hydrophilic, or amphipathic molecules, proteins, peptides, cell membrane components, and/or other biological components on the packaging exterior (see for example U.S. Pat. Nos. 5,589,563, 6,770,725, 7,884,171, 8,012,587, and 8,005,526, the entire contents of which are herein incorporated by reference). The packaging can further contain anti-microbial compositions and/or be sterilized (see for example U.S. Patent Publication Nos. 20050008676, 20100285084, 2009023270, the entire contents of which are herein incorporated by reference).

Figure 4A:
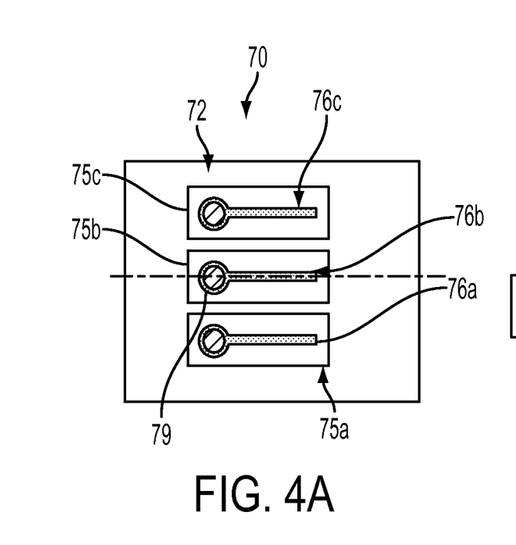
FIGS. 4A-4C depict operation of a MEMS cantilever exposing and hiding biologically active excitor in the biochip 10 of FIG. 2A.
Figure 4B:
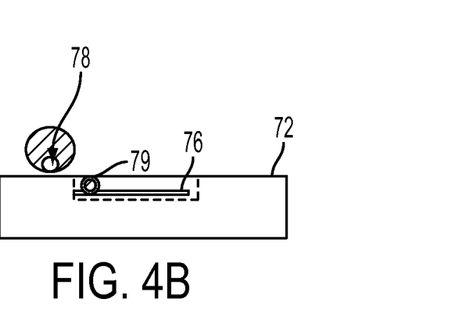
Figure 4C:
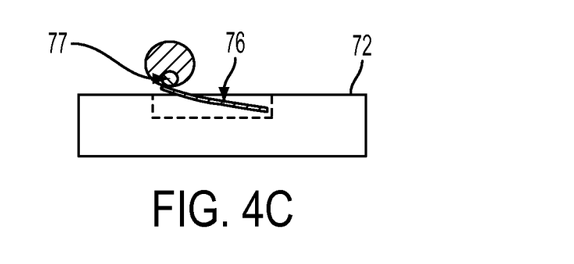

In one example, the configured elements on a surface of a substrate or wafer 12 include MEMS (Micro-Electro-Mechanical Systems) devices, and other semiconductor devices, such as active and passive semiconductor devices and systems. FIGS. 4A-4C show MEMS operation. The MEMS cantilever arm is situated on the external surface of the outer layer so that the arm can extend out externally from the package.

Further provided is an input connector device 25 adapted for receiving a patient's biological fluid, such as whole blood or lymph. Such input connectors are known in the art. The input connector 25 permits biological fluid or fluid communication with a patient's tissue. An optional membrane or screen filter can be included to keep the device from clogging, in which case the pump could, periodically or under pressure monitoring, reverse flow to relieve the membrane/screen of debris. Input connector 25 is in fluid communication between patient's biological fluid and/or tissue and a micro-fluidic pump element 37 mounted within or on wafer 23 within packaging 75 for receiving the biological fluid and pumping the biological fluid via channels to a series connection of interconnected chambers or reaction wells 30, 32, 34, 36, 38 within which chemical reactions, filtering, analysis and/or other treatment of the biological fluid is performed.

The input connector device 25 can be adapted to draw additional biological materials from the patient to self-renew storage of hormones, chemicals, etc. by providing a means to transport the stimulating species up its concentration gradient, i.e., from a region of lower concentration (outside the device) to a region of higher concentration (inside the device). As described in U.S. Patent Publication No. 20060009805, the entire contents of which are incorporated by reference herein, selective transport can be achieved using any of a variety of specific molecular carriers that reversibly form a complex with the chemical of interest and translocate it into the device. The biochip power supply is sufficient to transport the desired species against its concentration gradient.

At least one barrier layer covers each chamber, to isolate the reacting component from biological components outside the chambers. The barrier layer can be selectively disintegrated or permeabilized to expose the reacting component to the biological fluid.

For example, to initiate a chemical reaction, the barrier layer on the chamber is removed or made permeable under control of the CPU. The biological fluid passes into the chamber 30 (by diffusion or active pumping by pump element 37 of fluid into chamber), contacts an enzymatic reagent within the chamber, reacts with the reagent, and the products pass out of the chamber 30 to a fluid output 40 connector. This process may be repeated numerous times by opening additional chambers 32, 34, 36, 38 and exposing fresh reagent, or by addition of more reagent from a reagent well 43 via a microchannel 41.

In another example, one or more sensors are located inside each chamber. The sensors are protected from the physiological environment until the barrier layer is removed or made permeable. Once the barrier is removed or made permeable, the sensors can detect the presence and/or quantity of molecules or the conditions in or near one or more chambers. Such sensors can be used, for example, in controlling and monitoring the release of molecules to or from the patient's biological fluid and/or tissue and other chemical release devices or the release of chemicals from chambers in the same device. The permeability of the barrier layer can be passively controlled, changing without any user intervention, or actively controlled, in which a device controller initiates an action which renders the barrier layer permeable. See, for example, U.S. Pat. No. 7,985,386, the entire contents of which are herein incorporated by reference.

Inter-connecting each fluid chamber 32, 34, 36, 38 is a conduit structure, such as fluid micro-channels 35, and one or more micro-pumps 37. Inter-connections of micro-channels may be configured as parallel connections, serial connections, or combined serial and parallel connections. An output fluid micro-pump 37 and output fluid channel 39 provides output fluid material from chamber 38 to a fluid output 40 connector, which outputs biological fluid, waste, or other materials, either into the patient tissue or adjacent fluid system (blood or lymphatic system), or connected to other biological fluid output for further analysis within or external to the patient. Treatment of patient's biological and/or reagent waste to denature, kill, or otherwise render harmless prior to return of waste stream to patient is anticipated. Inclusion of a waste treatment chamber in which the waste stream can be exposed to heat, electric shock, ultrasonic or radiative energy to render the waste products harmless is taught.

Further included within packaging 75 of module 10 is one or more containers 43, e.g., a vessel or well, for carrying a gas, a chemical, or a reagent, each of which are connected to reaction chambers 32, 34, 36, 38 via microchannels 41 in fluid connection with a pump 47 for pumping controlled amounts of reactants/reagents necessary to stimulate a reaction in one or more chambers, e.g., a reactant vessel or tank 48. A control device, a central processing unit (CPU) or controller controls the actuation of the micro-pumps 37 such that a reagent, e.g., a gas or chemical from a well 43 or like vessel, may be released or transported into a reaction well or chamber. A further waste storage vessel or well 44 is in further fluid communication with chambers 32, 34, 36, 38 via microchannels 41 for receiving waste products or other materials, e.g., fluids, gases, from reactions. The CPU or controller may control the configuration of connections of fluid channels to/from the micro-pumps to reaction chambers 32, 34, 36, 38 and control the timing of reactive and reaction product material transfers to/from reaction chambers 32, 34, 36, 38. Chamber sizes can range from 1 cc to 300 cc, preferably between 10 to 100 cc.

In one embodiment, the CPU may be used to initiate a controlled release of a material, e.g., medicine, therapeutic agent, etc.

Figure 3:
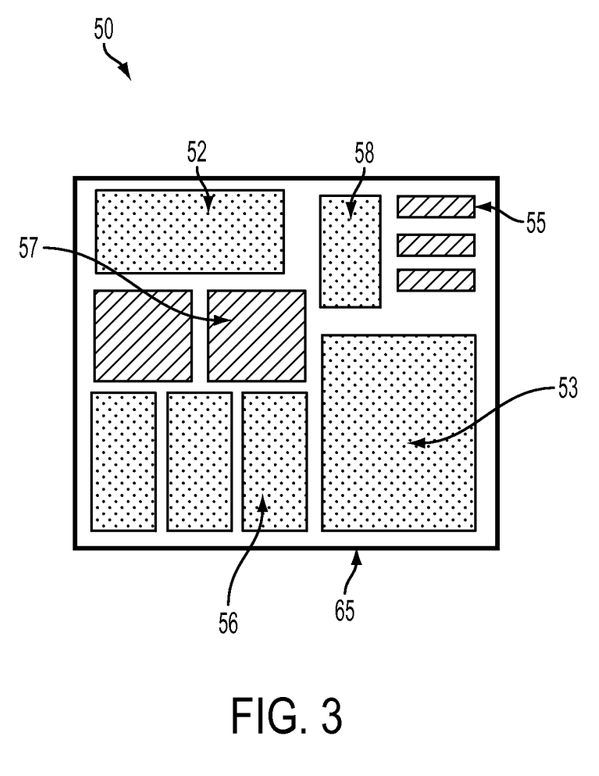
FIG. 3 depicts, in one embodiment, an IC controller unit 50 for biochip 10 including on-chip components formed on a wafer substrate.

In one embodiment, configured elements formed on substrate 12 include an Integrated Circuit (IC) controller unit or system 50 for controlling on-chip sensing, measuring and driving functions/operations performed. FIG. 3 depicts, in one embodiment, an IC controller unit 50 including on-chip components formed on a wafer substrate including but not limited to: a processing core including a Central Processing Unit (CPU) or like programmable controller and associated cache memory 53, a memory system including a Random Access Memory (RAM) 56. The memory system alternately, or in addition, may include DRAM or SRAM devices, or both, or other memory devices such as flash and EEPROM. Further located on substrate 12 are sensors 55 for performing one or more sensing and measuring functions such a measurement of temperature or pressure and/or sensors 57 for performing other sets of functions, such as chemical, biochemical or physiological measuring (for example measuring $O_2$, $CO_2$, urea, hormones, or proteins in biological fluids and/or tissues), radiation level measuring, or sensing the rate of local tissue mitosis or other tissue changes such as fibrosis, apoptosis or necrosis. The biochips module may be equipped with on the order of 10-10,000 sensor devices, depending upon the IC footprint.

Additionally, on the wafer 12 are formed preformed modules and other devices, such as a data bus (not shown) and a communications sub-system, e.g., including a receiver/transceiver device including a communications front-end 52 which may include a radio frequency (RF) transceiver or like functional transmitter/receiver devices performing communications with external devices, e.g., transmitting real-time sensor measurement data relating to on-biochip operations to an external monitor or a display of a host system. The transceiver can have a low power electromagnetic (EM) send function, for example, transmitting EM passband of about 200 to 1500 nm (UV to IR), and/or (Very Low Frequency) VLF to (Ultra high frequency) UHF wavelengths. The transceiver can have a low power sonic send function, transmitting or receiving sonic frequency bandwidth of less than 10,000 Hz, preferably less than 5,000 Hz, even more preferably less than 1,000 Hz. A data-rate generator, a Modulator, controller, write data generator block 58, and an RF antenna or similar communications device 65 operative with the transceiver (or separate receiver/transmitter devices) for receiving external commands or instruction signals, e.g., from a host, and communicating signals to module 10 for external processing. Antenna 58 further functions to passively receive electrical energy, and couple energy to a rectifier device (not shown) which may rectify the energy signals to obtain power for powering one or more configured components. Thus, module 10 may be powered by induction or RF coupling.

In one embodiment, a communications transceiver of module device 10 may implement short-wavelength radio transmissions according to the IEEE 802.x protocol (e.g., at industrial, scientific and medical (ISM) radio bands (portions of the radio spectrum) between 2400-2480 GHz). Thus, a network topology may be configured wherein two or more biochip modules communicate over a network, e.g., using IEEE 802.x or I.E.E.E 802.15.1 communications protocol, to an external host, and/or communicate with each other.

In further embodiments, a separate acoustic (ultrasonic) signal communications device may be formed on wafer or provided within the chip, e.g., for receiving or sending ultrasonic frequency communications. For example, a sensor device located within the package may include an acoustic pick-up that can receive instructions from a host at ultrasonic frequencies. Ultrasonics may be used in one implementation for mitosis rate sensing functions. For example, tissue deltas (such as changes in tissue density, temperature, cell size, disappearance of nuclei, and/or organizational characteristics) during mitosis are detectable by changes in ultrasonic (broad or narrow band) response as can be measured, for example, by sound wave transmission through tissue, sound wave reflection back from tissue, and/or spatial wavelength shifts. Tissue deltas can be based on measurements of the same (i.e., internal delta) target tissue at different times (for example, for a target liver, following surgical tumor removal, during chemo/radiation therapy and over a post-therapeutic monitoring period, measurements of tissue deltas can be periodically taken), or it can be based on changes between target tissue and a control tissue mass (external delta) at the same time (for example, target organ is liver and control tissue mass is a lung and both are continuously monitored until a triggering delta is encountered). It is understood that, while ultrasonic frequency signals may be received by the host system, e.g., instructions or commands, the responsive communications may be any generic RF communications such as 802.x protocol or preferably via IEEE 802.15.6 Body Area Networks (BAN), or via ultrasonic means for example, and vice versa (receive RF signal commands and respond with ultrasonic frequency signals).

FIG. 2B shows a cross-sectional view of biochip module 10 taken from line 2B-2B of the module 10 shown in FIG. 2A. In one embodiment, biochip module 10 is a stacked arrangement 80 including a first wafer layer 82 providing the interconnecting electrical conductor layers for routing of power, I/O signals control signals, etc. and power signal routing network for delivering power to configured elements of substrate 12. Biochip module 10 additionally includes a second wafer layer 84 having the formed reaction chambers 30, 32, 34, 36, 38, the reactant stores and waste product vessels, fluidic interconnects 35 and micro-pumps 37. Biochip module 10 further includes a third wafer layer 86 having configured elements such as the CPU, memory, sensor devices and communications circuits and MEMs circuits and devices. The wafer may optionally include a container 87 of radioactive materials, for example a radionuclide including but not limited to: a single radionuclide, or a plurality of different radionuclides to kill cancer cells. The radionuclide material function by emitting alpha (or beta) particle radiation and is shielded from the body, so the effluent (i.e., blood or other biological fluid) potentially containing cancer cells would be vectored to the shielded chamber, e.g., by a valve and channels means in fluid communication between said shielded chamber and the device input or previous chamber.

The biochip module can be implanted or administered to a fixed position in a subject, such that the biochip remains stationary within the subject's body. Alternatively, the biochip can be administered to a subject in a mobile or variable condition, such that the biochip moves from one position in the subject's body to a different position in the subject's body over a period of time, for example, in the bloodstream, lymphatic system, or other fluid movement system such as digestive tract. As used herein, to "administer" the biochip means to place the biochip within the subject, such as by oral, surgical, or injectable methods.

The biochip can be configured to act as an independent or interdependent biochip. As an independent or "stand-alone" unit, the biochip functions independently of any other biochips which may be administered to the patient. The independently-functioning biochip can have integrated function and/or communication with one or more sources external to the subject, e.g., a host monitoring system. As an interdependent or "systemic" unit, the biochip functions or communicates, e.g., via IEEE 802.x protocol, in tandem with one or more additional biochips administered to the subject. A plurality of interdependent biochips can be administered simultaneously with, prior to, or subsequent to administration of other biochips. Interdependent biochips can have integrated function and/or communications with one or more sources external to the subject, alternatively or in addition to biochip inter-functionality. A biochip "system" or plurality of biochips within the subject can be 2, 3, 4, 5, 6, 7, 8, 9, 10, 12, 15, 18, 20, 25, 30, 35, 40, 45, or 50 or more biochips that function together. The teaching is agnostic with respect to network architecture and/or topology.

The biochip can be configured for afferent/physiologic sensing operations. The biochip can alternatively be configured for efferent/driving operations.

Afferent/Sensing Functions.

Biochips of the variety described herein with respect to FIGS. 2A, 2B, 3 and 4, have sensing functions and, via the RF front end under CPU control, report signals and/or data back to the host or an external system, e.g., for monitoring or data analysis. In one example, an independent, stationary biochip with one or more sensing functions is provided. In another example, a plurality of interdependent, stationary biochips with interconnected sensing functions is provided. In a further example, an independent, mobile biochip with one or more sensing functions is provided. In an additional example, a plurality of interdependent, mobile biochips with interconnected sensing functions is provided.

For example, sensing biochips can sense $O_2$ in a patient's tissues and upload that data to the doctor via a specific communications channel; or the sensing biochip can function as an afferent nerve signal bridge by receiving signals from viable nerve cells in a patient and transmitting those signals, e.g., via RF or sonic communications, to a further point in the patient's healthy neurological network for communication with the patient's central nervous system (CNS) in cases where the patient has a nerve pathway gap. The biochip can employ a sonic and/or EM signal and a second biochip or a detector outside the patient can measure tissue response employing the Doppler effect (with spectrum spreading changes identified as proportional to tissue changes and/or indirectly via blood flow to targeted tissue). For example, one of two biochip modules in a networked topology surrounding the tissue whose mitosis rate is being monitored, may direct monochromatic electromagnetic wave signals (coherent at the source biochip module) through tissue being monitored for mitosis sensing for receipt at the second biochip module. The second biochip module may be configured to detect wave velocity spread and consequently phase shifts of the wave components of the source signal to detect mitosis rates. At a minimum, use of the Doppler effect (which may be in the acoustic range, such as Acoustic Doppler Velocimetry, etc.) can enable distinguishing high mitosis rates from regular mitosis rates directly due to tissues changes or indirectly due to increased blood flow to target tissue. Doppler effect can be used to indirectly assess mitosis rate of a tissue by velocimetric measurement of blood flow to the target tissue; in addition, spectrum spread aspects of Doppler can directly indicate tissue state changes by measuring deltas in velocities and/or phase shifts in signals of different wavelengths. For example, tissue changes can affect a signal's propagation differently at different wavelengths; in the case of capacitance or dielectric constant, the effect on a signal is different at different wavelengths. This could be accomplished as well by a single biochip module in a reflection mode in which a single signal source (i.e., the biochip) sends out a signal, and a target reflects a portion of the incident signal back towards the source; the source receiving and analyzing the returned signal. This is in contrast to the conjugate transmissive mode of operation in which two (or more) chips are involved: one is the signal source and the other is the signal receiving device, and the signal receiving device analyzes the received signal. In both modes, transmission of the signal through target tissue (and back where applicable) causes changes in the signal which the receiving device analyzes against established (i.e., modeled) results so that a target tissue assessment/evaluation/determination/diagnosis can be made.

In one example, a stationary, independent biochip is administered to a fixed position within the subject for afferent/sensing functioning. Sensing functions for this biochip can include measurements of physiologic temperature (T), pressure (P), intravenous (I-V) concentrations, and/or chemical/biochemical concentrations (such as $O_2$, $CO_2$, urea, or proteins).

Such a biochip can function as a dosimeter, providing pharmocologic chemical measuring or radiation measuring. This biochip can also function in sensing mitosis, fibrosis, or necrosis. This biochip can alternatively function in sensation of nerve pathways/proprioception.

In another example, a plurality of stationary biochips with interdependent or interconnected functionality is administered to a fixed position within the subject for afferent/sensing functioning. Under on-chip CPU or like controller device control, sensing functions for these biochips can include measurements of physiologic temperature (T), pressure (P), intravenous (I-V) concentrations, and/or chemical/biochemical concentrations (such as $O_2$, $CO_2$, urea, or proteins).

Interconnected biochips can function as a dosimeter, providing pharmocologic chemical measuring or radiation measuring. The biochips may also function in sensing mitosis, fibrosis, or necrosis and can alternatively function in sensation of nerve pathways/proprioception.

An afferent biochip or plurality of biochips can be designed to measure dynamically changing patient physical characteristics in local tissue, such as temperature, pressure, and/or electrical characteristics, or biochemical characteristics such as $O_2$, $CO_2$, protein concentrations, glucose, or drug or radiation delivery (x-ray, Beta or other radiation forms) at target organs or tissues. In a similar manner, the biochip or biochips can be designed to sense drug bioavailability and pharmacokinetics in local tissue, such as chemotherapeutic agents or other drug concentrations. The biochip or biochips can store and/or report observed data on-demand or on a preprogrammed periodic basis. The mode of sensing and/or communications can be enabled by devices adapted to provide sonic communication or sonic or EM communication using the Doppler Effect.

In one example, independent or interdependent stationary sensing biochips are implanted in a target tissue. The implanted biochips are powered by induction, RF coupling, or a combination of the two. The biochips are designed to interface with the tissue either passively, such as by measuring electrical or chemical activity in or adjacent to the tissue, or actively, such as by emulation of neural, chemical, or hormonal signaling pathways.

In a specific example, one or more independent or interdependent stationary sensing biochips are implanted in or adjacent to a tumor site for real-time monitoring of chemotherapeutic, drug or radiation delivery directly to the tumor. In a similar example, the biochip or biochips are implanted in or adjacent to a tissue with a non-cancerous condition for which treatment is sought, for the purpose of monitoring drug delivery to the tissue.

Sensing stationary biochips as disclosed herein can be designed to sense the rate of local tissue mitosis or other tissue changes such as fibrosis or necrosis.

For example, a single biochip implanted in a tumor or elsewhere in a patient's body can measure the real-time dynamic activity of the tumor or other tissues via a variety of means, including: monitoring and measuring ambient signals; transmitting sonic "pings" and reading reflected signals; measuring changes in electrical permittivity, magnetic permeability, turbidity, light transmission or reflection of light based on tissue changes, density or pressure by sonic energy and/or ultrasonics; monitoring blood or other biological fluid borne tumor marker concentrations; radiographic measurements, such as deploying radiolabels which would be taken-up by mitotic cells and measuring tissue radioactivity.

Figure 5:
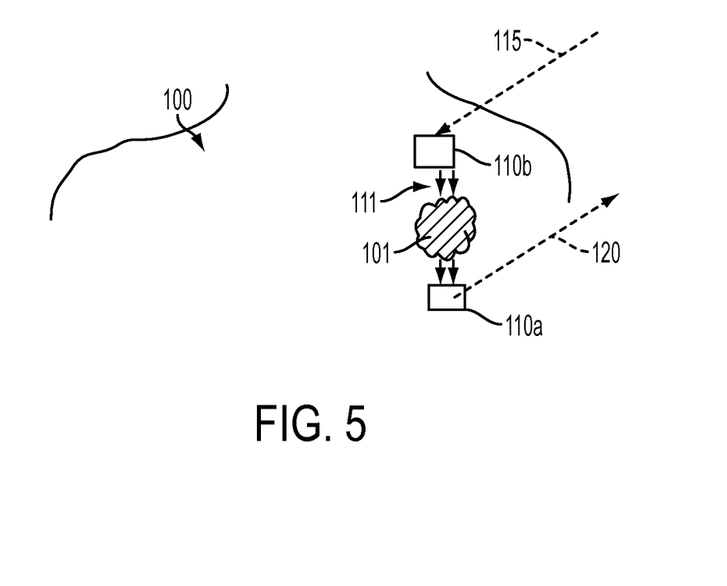
FIG. 5 shows an embodiment of mitosis rate sensing scheme for a patient implementing two interdependent biochips implanted in a patient's body in a transmissive mode of operation.

In another example, a plurality of interdependent biochips implanted in a tumor or elsewhere in a patient's body can measure the real-time dynamic activity of the tumor or other tissues. For example, FIG. 5 shows an embodiment of mitosis rate sensing scheme for a patient implementing two interdependent biochips implanted in a tumor or elsewhere in a patient's body 100. As shown in FIG. 5, a first biochip module 110a having one or more mode measurement sensor devices may be affixed located at or proximate the tissue 101 being monitored in a subject while an additional biochip module 110b in communication with the first module 110a provides a stimulus signal 111 (i.e., ultrasonic signals, monochromatic light signals, etc.) for receipt by the first sensor module 110a for sensing the stimulus signal or aspect of the tissue 101 being monitored. For example, via interchip send-receive mode measurements between chips 110a, 110b of electrical permittivity, magnetic permeability, turbidity, light transmittivity (reflection of light based on tissue changes), and density or pressure by sonic energy and/or ultrasonics, a mitosis rate condition may be deduced. The mitosis rate sensing scheme may occur at a programmed time interval, or, when instructed by a received external command signal 115, for example. Moreover, the sensor 110b performing the measuring may wirelessly communicate the data or information 120 to a host system, where the measurement is as described above for measuring tissue deltas. Increases in tissue volume and/or density indicate increased mitosis is occurring in that area.

Sensing stationary biochips as disclosed herein can alternatively be designed to sense, or sense and transmit, afferent neural signals, such as proprioceptive signals. Such neural biochips can be implanted or wearable.

In a further example, an independent, mobile biochip with one or more sensing functions is provided. Rather than being present in a fixed position within the subject's body, this biochip moves within the subject's body. Since the biochip is mobile (for example, floating within the blood, lymph or other biologic fluid), limitations of size to ensure no ischemia (blood flow blockage to tissues) require this biochip to be less than 5 microns in diameter in any direction, which permits clearance of capillaries. Due to size limitations, a mobile biochip is therefore limited to a single or few measurement function(s). Additionally, the size limitation necessitates that the biochip have no battery or integrated power source; instead, power is continuously fed to the biochip thru inductive or RF coupling. Sensing functions for this biochip can include measurements of physiologic temperature (T), pressure (P), intravenous (I-V) concentrations, or chemical/biochemical concentrations (such as $O_2$, $CO_2$, urea, or proteins). Such a biochip can function as a dosimeter, providing pharmocologic chemical measuring or radiation measuring. This biochip can alternatively function in sensing mitosis, fibrosis, or necrosis, or in sensation of nerve pathways/proprioception.

In an additional example, a plurality of interdependent, mobile biochips with interconnected sensing functions is provided. As with the single biochip, these biochips move within the subject's body and are therefore less than 5 microns in diameter in any direction, which permits clearance of capillaries. Due to size limitations, the mobile biochips are limited to a single measurement function and have no battery or integrated power source; instead, power is continuously fed to the biochips thru inductive or RF coupling. Sensing functions for these biochips can include measurements of physiologic temperature (T), pressure (P), intravenous (I-V) concentrations, or chemical/biochemical concentrations (such as $O_2$, $CO_2$, urea, or proteins). Interconnected biochips can function as a dosimeter, providing pharmocologic chemical measuring or radiation measuring. The biochips can alternatively function in sensing mitosis, fibrosis, or necrosis, or in sensation of nerve pathways/proprioception.

In one embodiment, signal and waveform conditioning are implemented. That is, received electrical signals may be generated, processed or conditioned for use as an efferent signal to target an organ or vessel, e.g., that is not responding to or does not respond well to patient's natural or conventional artificial electrical stimulus. For example, in the case of biochips functioning as an afferent nerve signal bridge, a biochip module functioning as bridge an attached to a healthy portion of a nerve ending may sense or receive an electrical stimulus either internal to the body, e.g., from the nerve itself, or, external from the body, via, an artificial RF instruction or command. The chip may respond by generating an appropriate efferent signal to drive the target organ, e.g., a muscle. This may involve processing or signal conditioning the responsive signal to be fired.

In a further application, a biochip "system" including a plurality of biochips may communicate to perform various coordinated functions. For example, communications and body area network (BAN) technologies may be established for use with the biochips according to an emerging IEEE 802.15.6 standard or other wireless protocol. In such embodiments, chips may act singly, for example, wirelessly communicating directly with a centralized communications function chip which communicates with the host. In this embodiment, a single node in the network controls communications between all biochips internally and externally to the host. Alternatively, the biochips can act in coordinated fashion, i.e., by wirelessly communicating directly amongst themselves and/or the host, within a network topology. In this embodiment, each node (address) communicates with any other and/or the external host (i.e., N-arbitrary parallel communication channels to the host).

Efferent/Driving Functions.

This disclosure further provides biochips with active functions that drive physiological activities. In one example, an independent, stationary biochip with one or more driving functions is provided. In another example, a plurality of interdependent, stationary biochips with interconnected driving functions is provided.

Driving biochips can be designed to emulate efferent nerve pathways, including emulation of neural firing and biochemical regulation of neural signaling. Alternatively, driving biochips can be designed to stimulate hormonal or other biochemical pathways.

In one example, a stationary, independent biochip is administered to a fixed position within the subject for efferent/driving functioning. Driving functions for this biochip can include emulation of efferent nerve pathways and stimulation of hormonal or other biochemical pathways.

In another example, a plurality of stationary biochips with interdependent or interconnected functionality is administered to a fixed position within the subject for efferent/driving functioning. Driving functions for these biochips can include emulation of efferent nerve pathways and stimulation of hormonal or other biochemical pathways.

For example, for a nerve bridging function, the biochip module may respond by enhancing the body's natural nerve "synapse" signal response that has been compromised. Alternately, the responsive signal generated may be conditioned to emulate the nerve signal itself. It is understood generally that, signals generated on-biochip that drive physiological activities, may be processed according to various user programmable parameters, including but not limited to: current and/or voltage signal amplitude, signal frequency or duty cycle, signal rise time, signal fall time, dwell time, etc., to yield the desired response. For the case of an afferent nerve bridge, the generated conditioned signal emulates the nerve signal for direct application to the muscle.

The biochips disclosed herein are capable of interfacing within the physiological environment of the subject. For example, biochips can assess the presence of hormones or other chemicals adjacent to the biochip by taking sample measurements, and deliver pharmaceutical or other beneficial substances to modulate, correct or improve physiological levels. In this manner, drugs, hormones, and other chemicals can be delivered appropriately and without the need for inconveniences such as external monitoring and injections. In one example, a biochip can measure blood sugar levels by regular monitoring of a subject's blood, and deliver a correct amount of insulin as needed in response to such measurements, thus eliminating the need for the subject to perform a needle prick and self-inject insulin.

In another example, proteins or fragments necessary to stimulate or inhibit a physiological reaction can be 'captivated' on the biochip by bonding the stimulatory or inhibitory aspect (such as a ligand) to the biochip. The biochip as provided herein has a means to 'expose' or 'hide' the protein to excite or suppress the activity. In one example, a biochip implanted proximal to a patient's thyroid has thyroid stimulating hormone (TSH) bound to an immovable phase on biochip. When the thyroid cells are receiving inadequate exposure to TSH and increases in T3 and T4 response hormones are desired, the biochip would 'expose' the TSH functional aspect to the follicular cells' TSH receptors, which would result in stimulating hormone production and secretion. When sufficient activity has been achieved (or alternatively, following a pre-programmed time limit), the biochip 'hides' the bound TSH and thyroid stimulation ceases.

Exposure or sequestration of proteins, etc. such as described herein can be performed by MEMS means that would open and close mechanical doors, and/or raise the molecule/compound to interface with the tissues by cantilever action following activation of the MEMS component of the biochip.

FIGS. 4A-4C depict operations of a MEMS cantilever exposing and hiding biologically active excitor in the biochip 10 of FIG. 2A. As shown in FIG. 4A, one or more MEMS devices 70 are formed on a Silicon device surface 72. Particularly, formed in the Silicon surface 72 are one or more MEMS devices, such as retractable MEMs cantilever-type devices 76a, 76b, 76c contained in a respective MEMS recession/cavity 75a, 75b, 75c associated with each MEMS device. While three MEMs cavities 75a, 75b, 75c receiving cantilever-type MEMs devices 76a, 76b, 76c are shown in the embodiment depicted in FIG. 4A, the module is not so limited. As shown in FIG. 4B, a MEMs cantilever-type device 76 in a relaxed state, hides a biologically active excitor molecule 79 (e.g., including an antibody, antigen, hormone, etc.) beneath a surface of the device surface 72 in a manner such that the excitor is shielded when recessed (e.g., by steric-hindrance). Prior to MEMs device activation, the cantilever device surface is exposed to a host or patient's material to be treated, e.g., a specific cell receptor 78, shown at or proximate the cantilever. As shown in FIG. 4C, upon receipt of an activation signal, e.g., such as a control signal generated by the CPU, or in response to activation by application of heat energy, the MEMS cantilever is deformed (stressed) to elevate the cantilever arm 76 and expose the excitor molecule beyond the chip boundaries for reaction with the host's receptor cell 78 such that the excitor-receptor complex 77 elicits a biological activity/response. This exposure may be autonomous, i.e., timed, or otherwise user controlled, via receipt of instruction signals, e.g., via external RF signal commands from the host system. Alternately, or in addition, a sensor device, which monitors certain functions, may trigger the excitation depending upon a sensed condition, e.g., to high or low a TSH level.

In another example, a MEMS means can have an integrated synthetic replica of a molecule of interest. A "template" of a protein or other efferent molecule can be produced as described in U.S. Patent Publication No. 2011/0021347, the entire contents of which are hereby incorporated by reference. This template can be used to create a synthetic equivalent of a desired molecule which would last for an extended period of time without needing replacement. The synthetic equivalent would be affixed to the cantilever arm, for example, and could be extended and retracted to produce a physiological response as needed.

Biochips as disclosed herein can interface with neural cells in the subject via electrical and/or biochemical interactions. For biochemical interactions, the biochip can assess the presence of ions (such as $Ca^{++}$) and/or neurotransmitters and respond by continuing the signal forward, or responding back to the signaling cells, utilizing stored ions, neurotransmitters, etc. For electrical interactions, the biochips are formed from, or coated with, either conductive materials or non-conductive materials with conductive dopants. These biochips can receive electrical signals from neurons and transmit electrical signals at appropriate levels. To further facilitate interactivity and reduce inflammatory reactions to the biochip, the packaging can be coated with a conductive polymer polymerized in the presence of live tissue, cells, cell constituents and/or in artificial scaffolds, as described in U.S. Pat. No. 8,005,526, the entire contents of which are incorporated by reference herein. Polymerization with live biological components increases the effective surface area of the biochip resulting in lowered impedance and enhanced biocompatibility thereby facilitating signal transduction. The biologically integrated packaging further stabilizes the electrically conductive substrate by interfacing the substrate with surrounding cells and/or tissue when implanted and can be loaded with bioactive substances that prevent the formation of unwanted immune rejections.

Biochips as provided herein include nano-scale biochips ("nanochips", defined as less than 5 microns in length in any dimension). The nanochips can be encapsulated in liposomes, or natural or synthetic semipermeable membranes. Alternatively, the nanochips can be inserted via known techniques into subject's host cells (such as RBCs, eosinophils, or macrophages) which optionally have been denucleated. The patient would be irradiated with EM (RF, microwave, etc.) or magnetic energy to power the encapsulated nanochips, which are designed to take readings and transmit data to an external system. The external system can read data and optionally correlate data readings to nanochip location within the subject's body, such as by internal 3D $O_2$ concentration mapping. Nanochips can have afferent or efferent functions. Afferent functions include measurement of conditions which can be sensed through a cell or liposome membrane, such as temperature, $O_2$ concentration, or glucose concentration.

Given the size of the nanochips, singulation is preferably achieved by employing semiconductor IC layout ground rules (GRs) with wide streets (large separation between dice in rows and columns). In this manner, nanoscale dice could be singulated. In addition, singulation could be done by lithographic introduction of features (such as lines or defects) into metallization, silicon, or other semiconducting substrate, whereupon cleavage along the fault or demarcation could occur following expression of some mechanical force, resulting in singulation of nano-sized biochips. In addition, alternating cycles of heat and cold could produce sufficient force to singulate nano-biochips along demarcations or fault lines.

As used herein, the terms "subject" and "patient" are used interchangeably and refer to an animal, preferably a mammal such as a non-primate (e.g., cows, pigs, horses, cats, dogs, rats etc.) and a primate (e.g., monkey and human), and most preferably a human.

Conditions treatable with the biochips as disclosed herein include but are not limited to kidney disease, liver dysfunction, pancreatitis, thyroid diseases, insulin resistance, paralysis due to severed or dysfunctional neurological pathways, and brain biochemical imbalances.

What is claimed is:

1. A biocompatible nanochip for treatment of a medical condition in a subject, the nanochip having a length, width and height dimension of less than 5 µm and comprising:
    a semiconductor substrate upon which is located:
    one or more sensor devices for sensing conditions and providing measurements within said subject,
    a programmed control unit and an associated memory block configured for controlling operations on said nanochip in response to received external command or a sensed condition within said subject; and,
    a communications sub-system including one or more communications devices for transmitting signals to and receiving signals from a communications receiver device external to said subject;
    a power source for powering said communications sub-system and said programmed control unit; and, an external biocompatible coating or covering for said semiconductor substrate.

2. The nanochip of claim 1, wherein the nanochip is implanted into a fixed position within the subject.

3. The nanochip of claim 1, wherein the microchip is mobile within the subject.

4. The nanochip of claim 2, wherein the nanochip is coordinated to operate in conjunction with one or more additional nanochips implanted into a fixed position within the subject.

5. The nanochip of claim 3, wherein the nanochip is coordinated to operate in conjunction with one or more additional mobile nanochips within the subject.

6. The nanochip of claim 1, wherein the nanochip is powered by inductive or radiofrequency coupling.

7. The nanochip of claim 1, wherein the medical condition is kidney disease, liver dysfunction, pancreatitis, thyroid diseases, insulin resistance, paralysis due to severed or dysfunctional neurological pathways, and brain biochemical imbalances.

* * * * *